US006191155B1

(12) United States Patent
Assmann et al.

(10) Patent No.: US 6,191,155 B1
(45) Date of Patent: Feb. 20, 2001

(54) ISOTHIAZOLCARBOXYLIC ACID DERIVATIVES

(75) Inventors: Lutz Assmann, Langenfeld; Dietmar Kuhnt, Burscheid; Hans-Ludwig Elbe, Wuppertal; Christoph Erdelen, Leichlingen; Stefan Dutzmann, Langenfeld; Gerd Hänssler, Leverkusen; Klaus Stenzel, Düsseldorf; Astrid Mauler-Machnik, Leichlingen, all of (DE); Haruko Sawada, Yuki; Haruhiko Sakuma, Oyama, both of (JP)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/554,170

(22) PCT Filed: Nov. 3, 1998

(86) PCT No.: PCT/EP98/06960

§ 371 Date: Jun. 5, 2000

§ 102(e) Date: Jun. 5, 2000

(87) PCT Pub. No.: WO99/24414

PCT Pub. Date: May 20, 1999

(30) Foreign Application Priority Data

Nov. 12, 1997 (DE) ..................... 197 50 011

(51) Int. Cl.[7] ..................... A01N 43/80; C07D 275/03

(52) U.S. Cl. ..................... 514/372; 514/236.8; 514/326; 514/342; 544/133; 546/209; 546/271.1; 548/214

(58) Field of Search ..................... 548/214; 546/271.1, 546/209; 514/372, 342, 236.8, 326; 544/133

(56) References Cited

U.S. PATENT DOCUMENTS 4,132,676 * 1/1979 Virgilio ..................... 252/522
5,240,951 * 8/1993 Shimotori et al. ..................... 514/372

FOREIGN PATENT DOCUMENTS

177097601 * 1/1972 (DE) .
19642529 * 4/1998 (DE) .
6-9313 1/1994 (JP) .

* cited by examiner

*Primary Examiner*—Laura E. Stockton
(74) *Attorney, Agent, or Firm*—Joseph C. Gil

(57) ABSTRACT

Novel isothiazolecarboxylic acid derivatives of the formula (I)

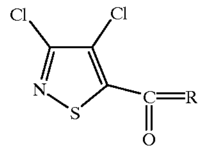

in which
R is as defined in the description,
a process for preparing the novel compounds and their use for protecting plants against attack by undesirable microorganisms and animal pests.

9 Claims, No Drawings

ISOTHIAZOLCARBOXYLIC ACID DERIVATIVES

This application is a 371 of PCT/E98/06960 filed Nov. 3, 1998.

The present invention relates to novel isothiazolecarboxylic acid derivatives, to a process for their preparation and to their use for protecting plants against attack by undesirable microorganisms and animal pests.

It is already known that numerous isothiazolecarboxylic acid derivatives have fungicidal properties (cf. U.S. Pat. No. 5,240,951 and JP-A 06-009 313). Thus, for example, isopropyl 3,4-dichloro-isothiazol-5-carboxylate can be used for controlling fungi. The activity of this compound is good, but in some cases leaves something to be desired at low application rates.

This invention, accordingly, provides novel isothiazolecarboxylic acid derivatives of the formula (I)

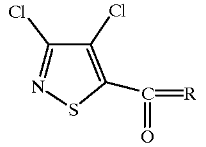

in which

R represents the groups —$OR^1$ or —$SR^2$ in which

- $R^1$ represents alkyl having 1 to 12 carbon atoms, where each of these radicals is mono- to trisubstituted by identical or different substituents selected from the group consisting of halogen, cyano, nitro, hydroxyl, carboxyl, alkoxy having 1 to 6 carbon atoms, halogenoalkoxy having 1 to 6 carbon atoms and 1 to 5 halogen atoms, alkylthio having 1 to 6 carbonatoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenylalkoxy having 1 to 4 carbon atoms in the alkoxy moiety and heterocyclylalkoxy having 1 to 3 hetero atoms, such as nitrogen, oxygen and/or sulphur, in the heterocyclyl moiety and 1 to 4 carbon atoms in the alkoxy moiety, or
- $R^1$ represents aryl having 6 to 10 carbon atoms which may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or
- $R^1$ represents aralkyl having 6 to 10 carbon atoms in the aryl moiety and 1 to 6 carbon atoms in the alkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or
- $R^1$ represents aroxyalkyl having 6 to 10 carbon atoms in the aryl moiety and 1 to 6 carbon atoms in the oxyalkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or
- $R^1$ represents optionally benzo-fused heterocyclylalkyl having 1 to 3 hetero atoms, such as nitrogen, oxygen and/or sulphur, in the heterocyclyl moiety and 1 to 6 carbon atoms in the alkyl moiety, where the heterocyclyl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy; or
- $R^1$ represents a radical of the formula

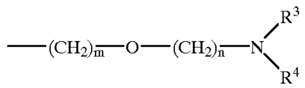

in which m and n independently of one another each represent integers from 1 to 3, $R^3$ represents alkyl having 1 to 4 carbon atoms or phenyl and $R^4$ represents hydrogen or alkyl having 1 to 4 carbon atoms, and

- $R^2$ represents alkyl having 1 to 12 carbon atoms, where each of these radicals may be mono- to trisubstituted by identical or different substituents selected from the group consisting of halogen, cyano, nitro, carboxyl, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenylalkoxy having 1 to 4 carbon atoms in the alkoxy moiety and heterocyclylalkoxy having 1 to 3 hetero atoms, such as nitrogen, oxygen and/or sulphur, in the heterocyclyl moiety and 1 to 4 carbon atoms in the alkoxy moiety, or $R^2$ represents aryl having 6 to 10 carbon atoms which may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms, alkylamino having 1 to 6 carbon atoms, dialkylamino having 1 to 6 carbon atoms in each alkyl moiety, phenyl and phenoxy, or $R^2$ represents aralkyl having 6 to 10 carbon atoms in the aryl moiety and 1 to 6 carbon atoms in the alkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents aroxyalkyl having 6 to 10 carbon atoms in the aryl moiety and 1 to 6 carbon atoms in the oxyalkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents optionally benzo-fused heterocyclylalkyl having 1 to 3 hetero atoms, such as nitrogen, oxygen and/or sulphur, in the heterocyclyl moiety and 1 to 6 carbon atoms in the alkyl moiety, where the heterocyclyl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents a radical of the formula

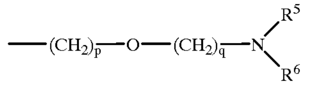

in which p and q independently of one another each represent integers from 1 to 3, $R^5$ represents alkyl having 1 to 4 carbon atoms or phenyl and $R^6$ represents hydrogen or alkyl having 1 to 4 carbon atoms.

Furthermore, it has been found that isothiazolecarboxylic acid derivatives of the formula (I) can be prepared by reacting 3,4-dichloro-isothiazole-5-carbonyl chloride of the formula (II)

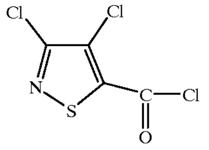

with compounds of the formula $$H—R \quad (III)$$

in which

R is as defined above, if appropriate in the presence of an acid binder and if appropriate in the presence of a diluent.

Finally, it has been found that the isothiazolecarboxylic acid derivatives of the formula (I) are highly suitable for protecting plants against attack by undesirable microorganisms. The compounds according to the invention are suitable both for mobilizing the defences of the plant against attack by undesirable microorganisms and as microbicides for the direct control of microorganisms. In addition, the compounds according to the invention are also active against animals which damage plants.

Surprisingly, the compounds according to the invention have better microbicidal activity than isopropyl 3,4-dichloro-isothiazole-5-carboxylate, which is a constitutionally similar prior-art compound having the same direction of action.

The formula (I) provides a general definition of the isothiazolecarboxylic acid derivatives according to the invention. Preference is given to compounds of the formula (I) in which R represents the groups $—OR^1$ or $—SR^2$ in which $R^1$ represents alkyl having 1 to 8 carbon atoms which is mono- to trisubstituted by identical or different substituents selected from the group consisting of fluorine, chlorine, bromine, cyano, nitro, hydroxyl, carboxyl, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenylalkoxy having 1 or 2 carbon atoms in the alkoxy moiety and five- or six-membered heterocyclylalkoxy having 1 to 3 hetero atoms, such as nitrogen, oxygen and/or sulphur, in the heterocyclyl moiety and 1 or 2 carbon atoms in the alkoxy moiety, or $R^1$ represents phenyl which may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^1$ represents phenylalkyl having 1 to 4 carbon atoms in the alkyl moiety, where the phenyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^1$ represents phenoxyalkyl having 1 to 4 carbon atoms in the oxyalkyl moiety, where the phenyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^1$ represents optionally benzo-fused five- or six-membered heterocyclylalkyl having 1 to 3 hetero atoms, such as nitrogen, oxygen and/or sulphur, in the heterocyclyl moiety and 1 to 4 carbon atoms in the alkyl moiety, where the heterocyclyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^1$ represents a radical of the formula

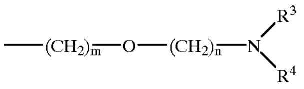

in which m and n independently of one another each represent 1 or 2, $R^3$ represents alkyl having 1 to 3 carbon atoms or phenyl and $R^4$ represents hydrogen or alkyl having 1 to 3 carbon atoms and $R^2$ represents alkyl having 1 to 8 carbon atoms which may be mono- to trisubstituted by identical or different substituents selected from the group consisting of fluorine, chlorine, bromine, cyano, nitro, carboxyl, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenylalkoxy having 1 or 2 carbon atoms in the alkoxy moiety and five- or six-membered heterocyclylalkoxy having 1 to 3 hetero atoms, such as nitrogen, oxygen and/or sulphur, in the heterocyclyl moiety and 1 or 2 carbon atoms in the alkoxy moiety, or $R^2$ represents phenyl which may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^2$ represents phenylalkyl having 1 to 4 carbon atoms in the alkyl moiety, where the phenyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^2$ represents phenoxyalkyl having 1 to 4 carbon atoms in the oxyalkyl moiety, where the phenyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^2$ represents optionally benzo-fused five- or six-membered heterocyclalkyl having 1 to 3 hetero atoms, such as nitrogen, oxygen and/or sulphur, in the heterocyclyl moiety and 1 to 4 carbon atoms in the alkyl moiety, where the heterocyclyl moiety may be mono- to trisubstituted by identical or different substituents selected from the group consisting of fluorine, chlorine, bromine, cyano, nitro, carboxyl, alkyl having 1 to 4 carbon atoms, halogenoalkyl having 1 to 4 carbon atoms and 1 to 3 fluorine, chlorine and/or bromine atoms, alkoxycarbonyl having 1 to 4 carbon atoms in the alkoxy moiety, alkoxy having 1 to 4 carbon atoms, halogenoalkoxy having 1 to 4 carbon atoms and 1 to 3 fluorine, chlorine and/or bromine atoms, alkylthio having 1 to 4 carbon atoms, halogenoalkylthio having, 1 to 4 carbon atoms and 1 to 3 fluorine, chlorine and/or bromine atoms, alkylamino having 1 to 4 carbon atoms, dialkylamino having 1 to 4 carbon atoms in each alkyl moiety, phenyl and phenoxy, or $R^2$ represents a radical of the formula

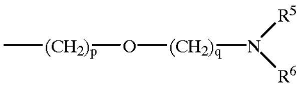

in which p and q independently of one another each represent 1 or 2, $R^5$ represents alkyl having 1 to 3 carbon atoms or phenyl and $R^6$ represents hydrogen or alkyl having 1 to 3 carbon atoms.

Particular preference is given to compounds of the formula (I) in which

R represents the groups $—OR^1$ or $—SR^2$ in which $R^1$ represents alkyl having 1 to 6 carbon atoms which is mono- to trisubstituted by identical or different substituents selected from the group consisting of fluorine, chlorine, bromine, cyano, nitro, hydroxyl, carboxyl, methoxy, ethoxy, isopropoxy, tert-butoxy, halogenoalkoxy having 1 to 3 carbon atoms and 1 to 3 fluorine, chlorine and/or bromine atoms, methylthio, ethylthio, halogenoalkylthio having 1 to 3 carbon atoms and 1 to 3 fluorine, chlorine and/or bromine atoms, methylamino, ethylamino, dimethylamino, diethylamino, benzyloxy or a radical of the formula $—O—(CH_2)_r—R^7$, in which r represents 1 or 2 and $R^7$ represents pyrrolidinyl, piperidinyl or morpholinyl, or $R^1$ represents phenyl which may be mono- to trisubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^1$ represents phenylalkyl having 1 or 2 carbon atoms in the alkyl moiety, where the phenyl moiety may be mono- to trisubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^1$ represents phenoxyalkyl having 1 or 2 carbon atoms in the oxyalkyl moiety, where the phenyl moiety may be mono- to trisubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^1$ represents a radical of the formula $—A—R^8$, in which A represents $—CH_2—$, $—CH_2—CH_2—$ or

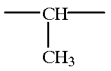

and $R^8$ represents pyrazolyl, imidazolyl, 1,2,4-triazolyl, pyrrolyl, furanyl, thienyl, thiazolyl, oxazolyl, pyridinyl, pyrimidinyl, triazinyl, 1,2,3-triazolyl, benzotriazolyl, quinolinyl, isoquinolinyl, quinazolinyl, indolyl, benzothienyl, benzofuranyl, benzothiazolyl or benzimidazolyl, where these radicals may be mono- or disubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^1$ represents a radical of the formula

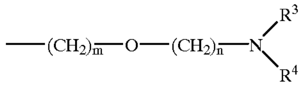

in which m and n independently of one another each represent 1 or 2, $R^3$ represents methyl, ethyl or phenyl and $R^4$ represents hydrogen, methyl or ethyl, and $R^2$ represents alkyl having 1 to 6 carbon atoms which may be mono- to trisubstituted by identical or different substituents selected from the group consisting of fluorine, chlorine, bromine, cyano, nitro, carboxyl, methoxy, ethoxy, isopropoxy, tert-butoxy, halogenoalkoxy having 1 to 3 carbon atoms and 1 to 3 fluorine, chlorine and/or bromine atoms, methylthio, ethylthio, halogenoalkylthio having 1 to 3 carbon atoms and 1 to 3 fluorine, chlorine and/or bromine atoms, methylamino, ethylamino, dimethylamino, diethylamino, benzyloxy and a radical of the formula $$—O—(CH_2)_s—R^9,$$

in which s represents 1 or 2 and $R^9$ represents pyrrolidinyl, piperidinyl or morpholinyl, or $R^2$ represents phenyl which may be mono- to trisubstituted by identical or different substituents selected from the group consisting of fluorine, chlorine, bromine, cyano, nitro, carboxyl, methyl, ethyl, propyl, isopropyl, n-butyl, sec-butyl, isobutyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^2$ represents phenylalkyl having 1 or 2 carbon atoms in the alkyl moiety, where the phenyl moiety may be mono- to trisubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamio, dimethylamino, diethylamino, phenyl and phenoxy, or $R^2$ represents phenoxyalkyl having or 2 carbon atoms in the oxyalkyl moiety, where the phenyl moiety may be mono- to trisubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio, halogenoalkylthio having 1 or 2 carbon atoms and 1 to 3 fluorine, chlorine and/or bromine atoms, methylamino, ethylamino, dimethylamino, diethylamino, phenyl and phenoxy, or $R^2$ represents a radical of the formula $$—A^1—R^{10},$$

in which $A^1$ represents $—CH_2—$, $—CH_2—CH_2—$ or

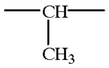

and $R^{10}$ represents pyrazolyl, imidazolyl, 1,2,4-triazolyl, pyrrolyl, furanyl, thienyl, thiazolyl, oxazolyl, pyridinyl, pyrimidinyl, triazinyl, 1,2,3-triazolyl, benzotriazolyl, quinolinyl, iso-quinolinyl, quinazolinyl, indolyl, benzothienyl, benzofuranyl, benzothiazolyl or benzimidazolyl, where these radicals may be mono- or disubstituted by identical or different substituents selected from the group consisting of fluorine, chlorine, bromine, cyano, nitro, carboxyl, methyl, ethyl, propyl, isopropyl, n-butyl, sec-butyl, iso-butyl, tert-butyl, halogenoalkyl having 1 or 2 carbon atoms and 1 to 3 fluorine, chlorine and/or bromine atoms, methoxycarbonyl, ethoxycarbonyl, methoxy, ethoxy, propoxy, isopropoxy, tert-butoxy, halogenoalkoxy having 1 or 2 carbon atoms and 1 to 3 fluorine, chlorine and/or bromine atoms, methylthio, ethylthio halogenoalkylthio having 1 or 2 carbon atoms and 1 to 3 fluorine, chlorine and/or bromine atoms, methylamino, ethylamino, dimethylamino, diethylamino, phenyl and phenoxy, or $R^2$ represents a radical of the formula

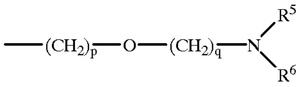

in which p and q independently of one another each represent 1 or 2, $R^5$ represents methyl, ethyl or phenyl and $R^6$ represents hydrogen, methyl or ethyl.

The radical definitions given above can be combined with one another as desired. Additionally, individual definitions may not be applicable.

Examples of compounds according to the invention which may be mentioned are the isothiazolecarboxylic acid derivatives of the formula (I) listed in the table below.

TABLE 1

(I)

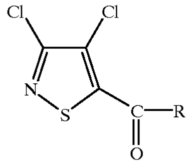

| R |
|---|
| $—O—CH_2—CH_2—CN$ |
| $—O—CH_2—CH_2—Cl$ |
| $—O—CH_2—CF_3$ |
| $—O—CH_2—CH_2—O—CH_3$ |
| $—O—CH_2—CH_2—CH_2—O—C_2H_5$ |
| $—O—CH_2—CH_2—S—C_2H_5$ |
| $—O—CH_2—CH_2—COOH$ |
| $—O—CH_2—CH_2—N(C_2H_5)_2$ |
| $—O—CH_2—CH_2—S—CF_3$ |
| 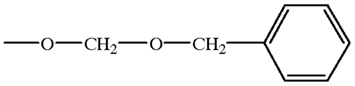 |
| 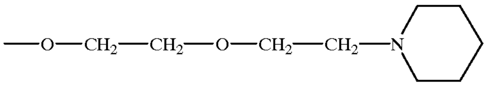 |
| 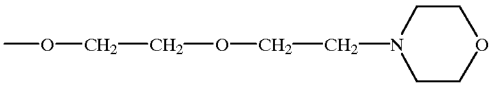 |
| 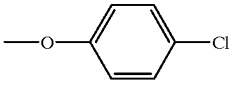 |
| 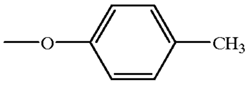 |
| 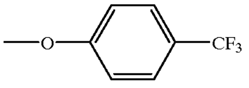 |

TABLE 1-continued (I)

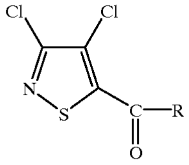

| R |
|---|
| 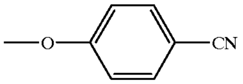 |
| 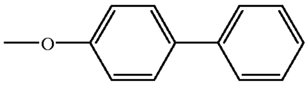 |
| 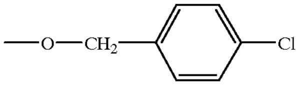 |
| 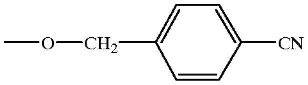 |
| 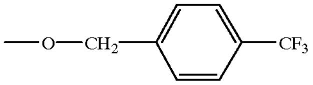 |
| 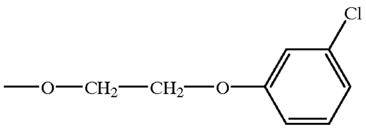 |
| 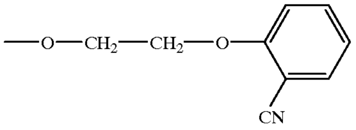 |
| 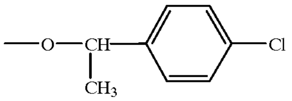 |
| 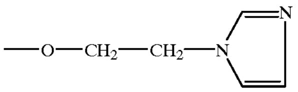 |
| 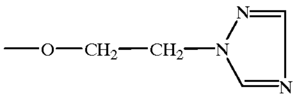 |
| $—O—CH_2—CH_2—O—CH_2—CH_2—N(C_2H_5)_2$ |
| $—O—CH_2—CH_2—O—CH_2—CH_2—N(CH_3)_2$ |

TABLE 1-continued
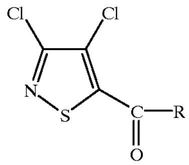
(I)
| R |
| --- |
| 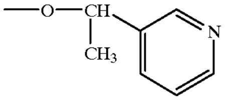 |
| 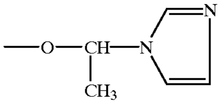 |
| $-S-CH_2-CH_2-CN$ |
| $-S-CH_2-CH_2-Cl$ |
| $-S-CH_2-CF_3$ |
| $-S-CH_2-CH_2-O-CH_3$ |
| $-S-CH_2-CH_2-CH_2-O-C_2H_5$ |
| $-S-CH_2-CH_2-S-C_2H_5$ |
| $-S-CH_2-CH_2-COOH$ |
| $-S-CH_2-CH_2-N(C_2H_5)_2$ |
| $-S-CH_2-CH_2-S-CF_3$ |
| 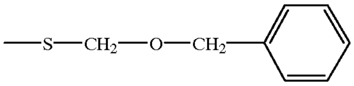 |
| 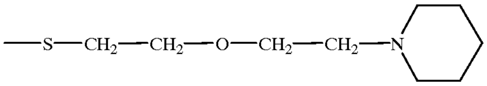 |
| 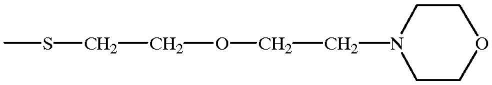 |
| 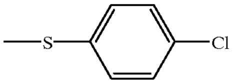 |
| 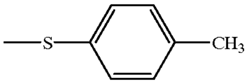 |
| 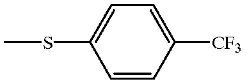 |
| 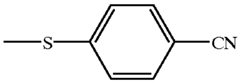 |
| 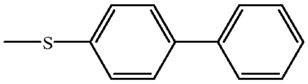 |
TABLE 1-continued
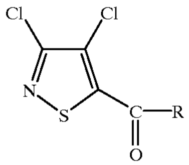
(I)
| R |
| --- |
| 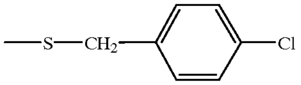 |
| 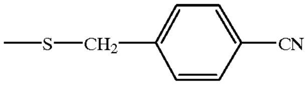 |
| 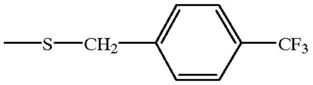 |
| 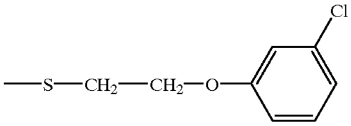 |
| 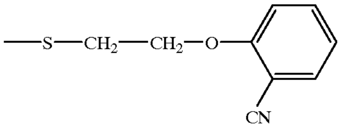 |
| 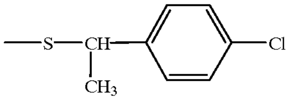 |
| 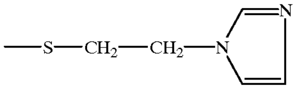 |
| 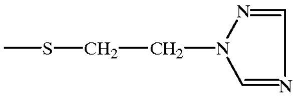 |
| $-S-CH_2-CH_2-O-CH_2-CH_2-N(C_2H_5)_2$ |
| $-S-CH_2-CH_2-O-CH_2-CH_2-N(CH_3)_2$ |
| 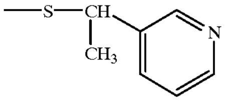 |
| 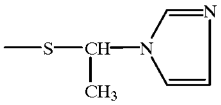 |
Using, 3,4-dichloro-isothiazole-5-carbonyl chloride and N,N-dimethylethanolamine as starting materials, the course of the process according to the invention can be illustrated by the equation below.

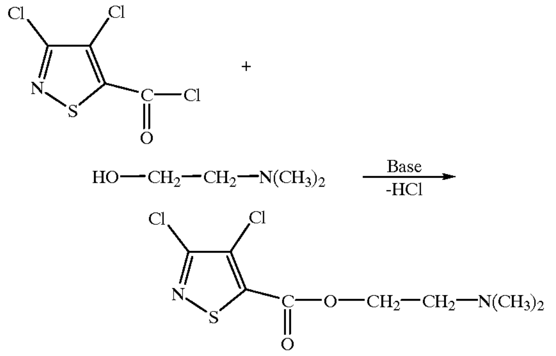

The 3,4-dichloro-isothiazole-5-carbonyl chloride of the formula (II) required as starting material for carrying out the process according to the invention is known (cf. U.S. Pat. No. 5,240,951).

The formula (III) provides a general definition of the alcohols and thioalcohols furthermore required as reaction components for carrying out the process according to the invention. In this formula, R preferably and in particular has those meanings which have already been mentioned in connection with the description of the substances of the formula (D according to the invention as being preferred and as being particularly preferred, respectively, for this radical.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate, furthermore ammonium hydroxide, ammonium acetate or ammonium carbonate, or tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process according to the invention are all inert organic solvents. Preference is given to using aliphatic, alicyclic or aromatic hydrocarbons, such as petroleum ether, hexane, heptane, cyclohexane, methyl cyclohexane, benzene, toluene, xylene or decalin; halogenated hydrocarbons, such as chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane.

When carrying out the process according to the invention, the reaction temperatures can be varied within a relatively wide range. In general, the reaction is carried out at temperatures between −10° C. and +150° C., preferably between 0° C. and 100° C.

The process according to the invention is generally carried out under atmospheric pressure. However, it is also possible to carry out the process under elevated or, if no volatile components participate in the reaction, under reduced pressure.

When carrying out the process according to the invention, generally 1 to 5 mol, preferably 1 to 2 mol, of the compound of the formula (III) and an equivalent amount or an excess of acid binder are employed per mole of 3,4-dichloro-isothiazol-5-carbonyl chloride of the formula (II). Work-up is carried out by customary methods. In general, the reaction mixture is concentrated after the reaction has ended, the residue that remains is admixed with water and an organic solvent which is only sparingly miscible with water, and the organic phase is separated off, washed, dried and concentrated. The product that remains can be freed of any impurities that may be present by customary methods.

The active compounds according to the invention have a potent plant-strengthening action. They are therefore suitable for mobilizing the defences of the plant against attack by undesirable microorganisms. In the present context, plant-strengthening compounds are those substances which are capable of stimulating the defensive system of plants in such a way that the treated plants, when subsequently inoculated with undesirable microorganisms, develop substantial resistance against these microorganisms.

In the present case, undesirable microorganisms are phytopathogenic fungi, bacteria and viruses. The compounds according to the invention can also be used to protect plants within a certain period of time after the treatment against attack by the abovementioned harmful organisms. The period of time for which protection is effected generally extends for from 1 to 10 days, preferably for 1 to 7 days, after the treatment of the plants with the active compounds.

In addition to the plant-strengthening action, the active compounds according to the invention also have potent microbicidal action and are additionally used in practice for directly controlling undesirable microorganisms. The active compounds are suitable for use as crop protection agents, in particular as fungicides.

In crop protection, the undesirable microorganisms include fungi from the classes of the Plasmodiophoromycetes, Oomycetes, Chytridiomycetes, Zygomycetes, Ascomycetes, Basidiomycetes, Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (Conidia form: Drechslera, syn: Helminthosporium);

Cochliobolus species, such as, for example, *Cochliobolus sativus* (Conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Alternaria brassicae;*

Pseudocercosporella species, such as, for example, *Pseudocercosporella herpotrichoides.*

The good crop safety of the active compounds at the concentrations required for controlling plant diseases permits a treatment of above-ground parts of plants, and also a treatment of propagation stock and seed and of the soil.

The active compounds according to the invention can be used here particularly successfully for controlling cereal diseases, such as, for example, against Erysiphe species, or of diseases in viticulture, fruit and vegetable growing, such as, for example, against Plasmopara or Venturia species, or of rice diseases, such as, for example, against Pyricularia species. The active compounds according to the invention also permit successful control of other plant diseases, such as, for example, Septoria, Cochliobolus, Pyrenophora and Pseudocercosporella species, and specific mention may be made of *Drechslera teres.*

The active compounds according to the invention are also suitable for increasing the harvest yield. Additionally, they have reduced toxicity and good crop safety. The active compounds according to the invention are also suitable for controlling animal pests, in particular insects, arachnids and nematodes, which are encountered in agriculture, in forests, in horticulture, in the protection of stored products and of materials, and also in the hygiene field and in veterinary medicine, and have good crop safety and favourable toxicity to warm-blooded animals. The compounds are active against normally sensitive and resistant species and against pests in all or some stages of development. The abovementioned pests include:

From the order of the Isopoda, for example, *Oniscus asellus, Armadinlidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flarnnea, Spodoptera litura,* Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura furniferana, Clysia ambiguella, Homona magnanima* and *Tortrix viridana.*

From the order of the Coleoptera, for example, *Anobium punctatum, Rhizopertha dorninica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderna spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,*

Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalonmma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus serrmipenetrans,* Heterodera spp., Globodera spp., Meloidogyne spp., Aphelenchoides spp., Longidorus spp., Xiphinema spp. and Trichodorus spp.

The compounds according to the invention can be employed particularly successfully for controlling plant-damaging mites, such as against the greenhouse red spider mite (*Tetranychus urticae*), or for controlling plant-damraging insects, such as against the caterpillars of the diamond-back moth (*Plutella maculipennis*), the larvae of the mustard beetle (*Phaedon cochleariae*), and the green rice leafhopper (*Nephotettix cincticeps*).

The compounds according to the invention also have herbicidal activity.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, liquefied pressurized gases and/or solid carriers, optionally with the use of surface-active agents, that is emulsifying agents and/or dispersing agents, and/or foam-forming agents. If the extender used is water, it is also possible to employ for example organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates. As dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be used as such or in their formulations, also as a mixture with known fungicides, bactericides, acaricides, nematicides, or insecticides, for example, to improve the activity spectrum or prevent the development of resistance. In many instances, synergistic effects are obtained, i.e. the activity of the mixture exceeds the activity of the individual components.

Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzarnacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimizone, fluazinam, flumetover, fluoromide, fluquinconazole, flurprimidol, flusilazole, flusulphamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procyrridone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-H-imidazole, 1-methyl-5-nonyl-2-(phenylmethyl)-3-pyrrolidinone, 2',6'-dibromo-2-methyl-4'-trifluoromethoxy-4'-trifluoro-methyl-1,3-thiazole-5-carboxamide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl )-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamiide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetanide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazoldinyl)-acetaride, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine-sodium salt, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran]-3'-one, Bactericides bromopol, dichlorophen, nitrapyrin, nickel dimethyldithiocarbamate, kasugamycin, octhilinon, furan-carboxylic acid, oxytetracycline, probenazole, streptomycin, tecloftalam, copper sulphate and other copper formulations.

Insecticides/Acaricides/Nematicides abamectin, acephate, acrinathrin, alanycarb, aldicarb, alphamethrin, amitraz, avermectin, AZ 60541, azadirachtin, azinphos A, azinphos M, azocyclotin,

*Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezin, cyanophos, cycloprothrin, cyfluthrin, cyhalothrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerat, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximat, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoat, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators, is also possible.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, scattering, dusting, foaming, spreading, etc. Furthermore, it is possible to apply the active compounds by the ultra-low-volume method or to inject the active compound preparation or the active compound itself into the soil. It is also possible to treat the seeds of the plant.

When using the active compounds according to the invention for controlling microorganisms, the application rates can be varied within a relatively wide range, depending on the kind of application. In the treatment of parts of plants, the active compound application rates are generally between 0.1 and 10,000 g/ha, preferably between 10 and 1000 g/ha. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

Likewise, when used against animal pests, the compounds according to the invention can be present in commercially available formulations and also in the use forms prepared from these formulations as a mixture with synergists. Synergists are compounds which increase the activity of the active compounds, without it being necessary for the added synergist itself to be active.

The active compound content of the use forms prepared from the commercial formulations can vary within wide ranges. The active compound concentration of the use forms may be from 0.0000001 to 95% by weight of active compound, preferably between 0.0001 and 1% by weight.

The application is carried out in a manner which is adapted to the use forms.

The preparation and the use of the active compounds according to the invention is illustrated by the examples below.

PREPARATION EXAMPLES

Example 1

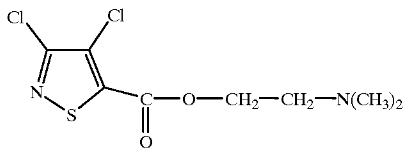

At 5 to 10° C., 77.37 g (0.3 mol) of 3,4-dichloro-isothiazole-5-carbonyl chloride are added dropwise with stirring over a period of 10 minutes to a mixture of 31 g (0.345 mol) of N,N-dimethyl-ethanolamine and 350 ml of pyridine. After the addition has ended, the reaction mixture is admixed with 260 ml of tetrahydrofuran and allowed to warm to room temperature and then stirred at room temperature for 2 hours. The reaction mixture is subsequently concentrated under reduced pressure. The residue that remains is stirred with 500 ml of water and 500 ml of ethyl acetate. The phases are separated and the aqueous phase is extracted once more with 300 ml of ethyl acetate. The combined organic phases are initially washed with 450 ml of aqueous sodium bicarbonate solution and then with 300 ml of aqueous sodium chloride solution and then concentrated under reduced pressure. The product that remains is admixed with ethyl acetate. The resulting precipitate is filtered off with suction and dried. This gives 1.17 g of a crystalline product of melting point 127 to 129° C.

From the aqueous phase that is initially obtained, a crystalline precipitate separates off, which is filtered off with suction and dried. This gives 22.35 g of a crystalline product of melting point 129 to 130° C.

After 48 hours of standing at room temperature, a solid separates off from the aqueous mother liquor once more, and this solid is filtered off with suction and dried. This gives 10.25 g of a crystalline product of melting point 128 to 130° C.

A total of 32.6 g (39.15% of theory) of (2-dimethylamino)-ethyl 3,4-dichloroisothiazole-5-carboxylate are obtained.

Preparation of the starting material:

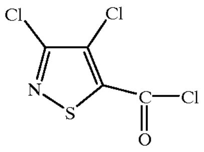

At room temperature, 146 g (1.23 mol) of thionyl chloride are added dropwise with stirring over a period of 5 minutes to 8.92 g (0.045 mol) of 3,4-dichloro-isothiazole-5-carboxylic acid. 4 drops of dimethylformamide are then added, and the reaction mixture is heated at reflux for one hour. The reaction mixture is subsequently cooled to room temperature and concentrated under reduced pressure. This gives 12.19 g of 3,4-dichloro-isothiazole-5-carbonyl chloride in the form of an orange oil.

The compounds of the formula (I) listed in the table below are also prepared by the method given above.

TABLE 2

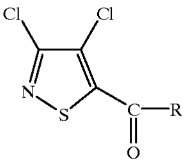

(I)

| Ex. No. | R | Physical constants |
|---|---|---|
| 2 | $-O-CH_2-CH_2-N(C_2H_5)_2$ | log P = 1.37*); λ = 234 nm**), 280 nm |
| 3 | 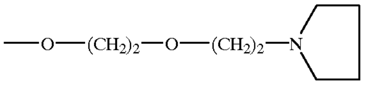 | log P = 1.36; λ = 240 nm, 288 nm |
| 4 | 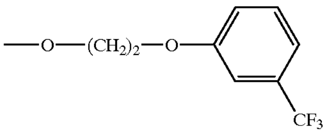 | log P = 4.71; λ = 222 nm and 289 nm |
| 5 | 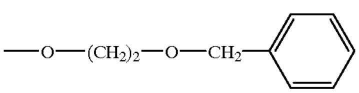 | log P = 4.12; λ = 238 nm and 288 nm |

TABLE 2-continued
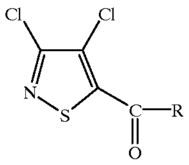
(I)
| Ex. No. | R | Physical constants |
|---|---|---|
| 6 | 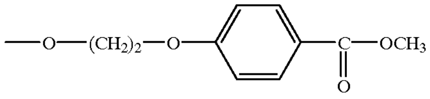 | log P = 3.91; λ = 252 nm |
| 7 | 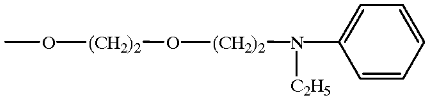 | log P = 2.60; λ = 240 nm and 288 nm |
| 8 | $-O-(CH_2)_2-O-CH_2CF_3$ | log P = 3.55; λ = 238, 240 and 288 nm |
| 9 | $-O-(CH_2)_2-O-CH(CH_2F)_2$ | log P = 3.11; λ = 238, 240 and 2288 nm |
| 10 | 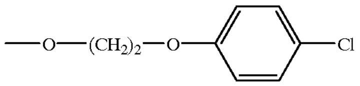 | log P = 4.58; λ = 228 nm and 286 nm |
| 11 | 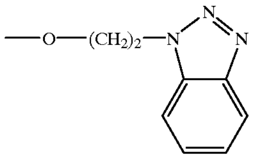 | log P = 2.81; λ = 204, 2.46 and 286 nm |
| 12 | 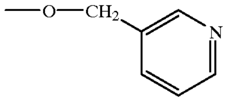 | m.p. = 70–71° C. |
| 13 | 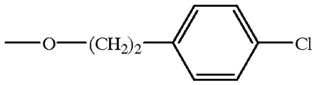 | m.p. = 103–105° C. |
| 14 | 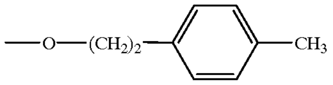 | m.p. = 64–65° C. |
| 15 | $-S-CH_3$ | log P = 3.46; λ = 252 nm and 288 nm |
| 16 | 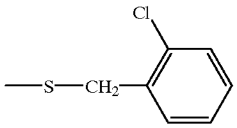 | m.p. = 60–61° C. |
| 17 | $-S-CH_2-CH(CH_3)_2$ | log P = 5.16; λ = 252 nm and 290 nm |
| 18 | $-S-C_3H_{7-n}$ | log P = 4.66; λ = 252 nm and 287 nm |
| 19 | 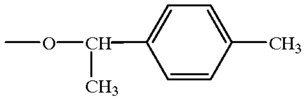 | log P = 5.02; λ = 239 nm and 287 nm |

TABLE 2-continued

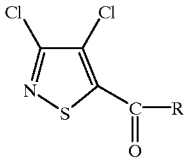

(I)

| Ex. No. | R | Physical constants |
|---|---|---|
| 20 | 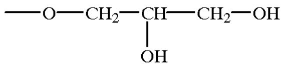 | log P = 1.49 |

*) The log P values were determined in accordance with EEC Directive 79/831 Annex V.A8 by HPLC (gradient method, acetonitrile/0.1% of aqueous phosphoric acid).
**) The λ values denote maxima in the UV spectrum.

Example A

Pyricularia Test (Rice)/Induction of Resistance

Solvent: 2.5 parts by weight of acetone

Emulsifier: 0.06 parts by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for resistance-inducing activity, young rice plants are sprayed with the preparation of active compound at the stated application rate. 5 days after the treatment, the plants are inoculated with an aqueous spore suspension of *Pyricularia oryzae.* The plants are subsequently placed in a greenhouse at 100% relative atmospheric humidity and a temperature of 25° C.

Evaluation is carried out 4 days after the inoculation. 0% means an efficacy which corresponds to that of the control, while an efficacy of 100% means that no infection is observed.

Active compounds, application rates and test results are shown in the table below.

TABLE A

Pyricularia test (rice)/Induction of resistance

| Active compound | Application rate of active compound in g/ha | Efficacy in % |
|---|---|---|
| According to the invention | | |
| 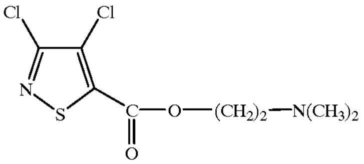 (1) | 750 | 90 |
| 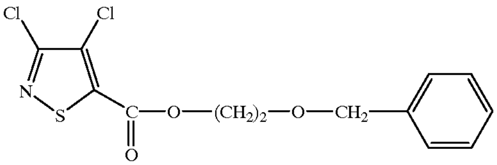 (5) | 750 | 80 |
| 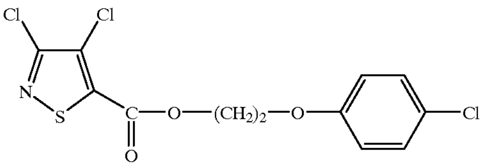 (10) | 750 | 70 |

TABLE A-continued
| Pyricularia test (rice)/Induction of resistance | | |
|---|---|---|
| Active compound | Application rate of active compound in g/ha | Efficacy in % |
| 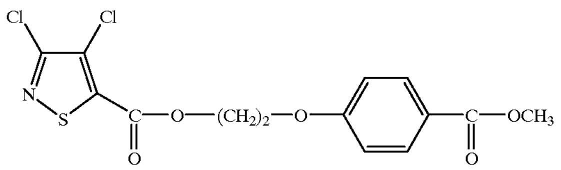 (6) | 750 | 90 |
| 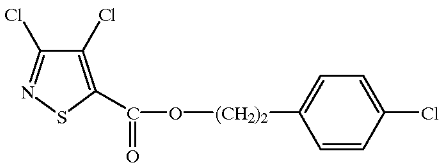 (13) | 750 | 100 |
| 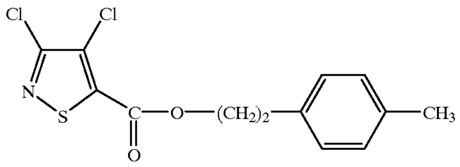 (14) | 750 | 100 |
| 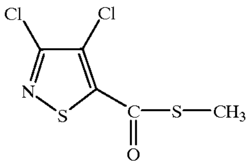 (15) | 750 | 90 |
| 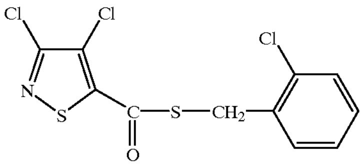 (16) | 750 | 90 |
| 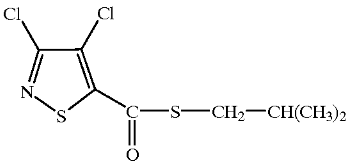 (17) | 750 | 100 |

TABLE A-continued

Pyricularia test (rice)/Induction of resistance

| Active compound | Application rate of active compound in g/ha | Efficacy in % |
|---|---|---|
| 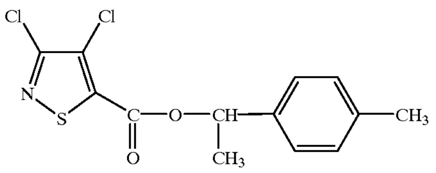 (19) | 750 | 90 |

Example B

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with caterpillars of the diamond-back moth (*Plutella xylostella*) while the leaves are still moist.

After 7 days, the kill is determined. An efficacy of 100% means that all caterpillars have been killed, while an efficacy of 0% means that none of the caterpillars have been killed.

Active compounds, active compound concentrations and test results are shown in the table below.

Example C

Erysiphe Test (Barley)/Protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, while an efficacy of 100% means that no infection is observed.

TABLE B plant-damagaing insects
Plutella test

| Active | Active compound concentration in % by weight | Kill in % after 7d |
|---|---|---|
| According to the invention | | |
| 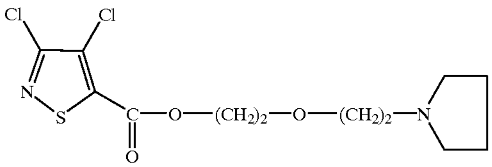 (3) | 0.1 | 100 |
| 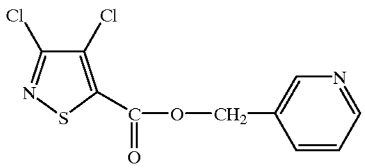 (12) | 0.1 | 100 |

Active compounds, application rates and test results are shown in the table below.

TABLE C

| Erysiphe test (barley)/protective | | |
|---|---|---|
| Active | Active compound concentration in % by weight | Kill in % after 7d |
| According to the invention | | |
| 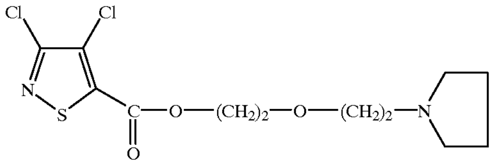 (3) | 250 | 100 |

Example D

*Leptosphaeria nodorum* Test (Wheat)/Protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature or approximately 15° C. and a relative atmospheric humidity of 80%.

Evaluation is carried out 10 days after the inoculation. 0% means an efficacy which corresponds to that of the control, while an efficacy of 100% means that no infection is observed.

Active compounds, application rates and test results are shown in the table below.

TABLE D

| Leptasphaeria nodorum test (wheat)/protective | | |
|---|---|---|
| Active compound | Applicaton rate of active compound in g/ha | Efficacy in % |
| According to the invention | | |
| 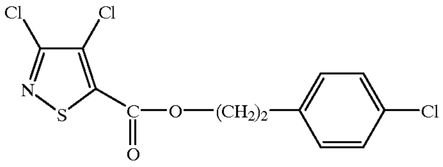 (13) | 250 | 81 |

What is claimed is:

1. An isothiazolecarboxylic acid derivatives of the formula

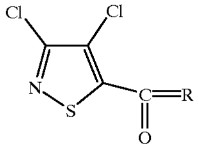

(I)

in which

R represents the groups —$OR^1$ or —$SR^2$ in which $R^1$ represents alkyl having 1 to 12 carbon atoms, where each of these radicals is mono- to trisubstituted by identical or different substituents selected from the group consisting of halogen, cyano, nitro, hydroxyl, carboxyl, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenylalkoxy having 1 to 4 carbon atoms in the alkoxy moiety and heterocyclylalkoxy having 1 to 3 hetero atoms in the heterocyclyl moiety and 1 to 4 carbon atoms in the alkoxy moiety, or $R^1$ represents aryl having 6 to 10 carbon atoms which may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^1$ represents aralkyl having 6 to 10 carbon atoms in the aryl moiety and 1 to 6 carbon atoms in the alkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^1$ represents aroxyalkyl having 6 to 10 carbon atoms in the aryl moiety and 1 to 6 carbon atoms in the oxyalkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^1$ represents optionally benzo-fused heterocyclylalkyl having 1 to 3 hetero atoms in the heterocyclyl moiety and 1 to 6 carbon atoms in the alkyl moiety, where the heterocyclyl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^1$ represents a radical of the formula

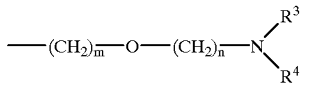

in which m and n independently of one another each represent integers from 1 to 3, $R^3$ represents alkyl having 1 to 4 carbon atoms or phenyl and $R^4$ represents hydrogen or alkyl having 1 to 4 carbon atoms, and $R^2$ represents alkyl having 1 to 12 carbon atoms, where each of these radicals may be mono- to trisubstituted by identical or different substituents selected from the group consisting of halogen, cyano, nitro, carboxyl, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenylalkoxy having 1 to 4 carbon atoms in the alkoxy moiety and heterocyclylalkoxy having 1 to 3 hetero atoms in the heterocyclyl moiety and 1 to 4 carbon atoms in the alkoxy moiety, or $R^2$ represents aryl having 6 to 10 carbon atoms which may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms, alkylamino having 1 to 6 carbon atoms, dialkylamino having 1 to 6 carbon atoms in each alkyl moiety, phenyl and phenoxy, or $R^2$ represents aralkyl having 6 to 10 carbon atoms in the aryl moiety and 1 to 6 carbon atoms in the alkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents aroxyalkyl having 6 to 10 carbon atoms in the aryl moiety and 1 to 6 carbon atoms in the oxyalkyl moiety, where the aryl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents optionally benzo-fused heterocyclylalkyl having 1 to 3 hetero atoms in the heterocyclyl moiety and 1 to 6 carbon atoms in the alkyl moiety, where the heterocyclyl moiety may be mono- to trisubstituted by identical or different substituents selected from the group consisting of halogen, cyano, nitro, carboxyl, alkyl having 1 to 6 carbon atoms, halogenoalkyl having 1 to 6 carbon atoms and 1 to 5 halogen atoms, alkoxycarbonyl having 1 to 6 carbon atoms in the alkoxy moiety, alkoxy having 1 to 6 carbon atoms, halogenoalkoxy having 1 to 6 carbon atoms and 1 to 5 halogen atoms, alkylthio having 1 to 6 carbon atoms, halogenoalkylthio having 1 to 6 carbon atoms and 1 to 5 halogen atoms, alkylamino having 1 to 6 carbon atoms, dialkylamino having 1 to 6 carbon atoms in each alkyl moiety, phenyl and phenoxy, or $R^2$ represents a radical of the formula

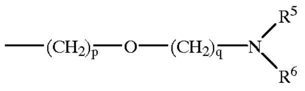

in which p and q independently of one another each represent integers from 1 to 3, $R^5$ represents alkyl having 1 to 4 carbon atoms or phenyl and $R^6$ represents hydrogen or alkyl having 1 to 4 carbon atoms.

2. An isothiazolecarboxylic acid derivative according to claim 1, characterized by the formula

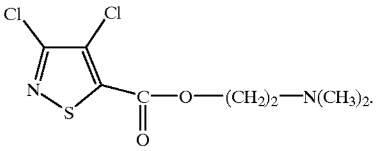

3. An isothiazolecarboxylic acid derivative according to claim 1, characterized by the formula

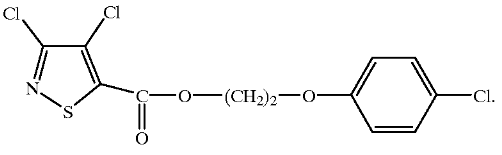

4. An isothiazolecarboxylic acid derivative according to claim 1, characterized by the formula

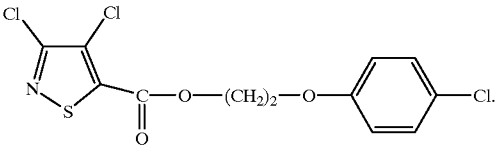

5. An isothiazolecarboxylic acid derivative according to claim 1, characterized by the formula

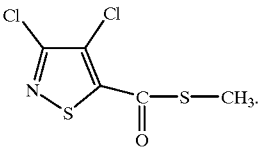

6. A composition for protecting plants against attack by undesirable microorganisms and animal pests comprising an active amount of at least one isothiazole carboxylic acid derivative of the formula (I) according to claim 1, in addition to an extender and/or a surfactant.

7. A method for protecting plants against attack by undesirable microorganisms and animal pests comprising applying an active amount of isothiazolecarboxylic acid derivative of the formula (I) according to claim 1 to the plants and/or their habitat.

8. A process for preparing an isothiazolecarboxylic acid derivative of the formula (I) according to claim 1, characterized in that 3,4-dichloro-isothiazole-5-carbonyl chloride of the formula (II)

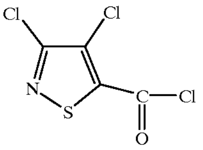

is reacted with compounds of the formula

H—R (III)

in which

R is as defined in claim 1, if appropriate in the presence of an acid binder and if appropriate in the presence of a diluent.

9. A process for preparing composition for protecting plants against attack by undesirable microorganisms and animal pests comprising mixing an isothiazolecarboxylic acid derivative of the formula (I) according to claim 1 with extenders and/or surfactants.

* * * * *